United States Patent [19]

Högberg et al.

[11] Patent Number: 6,124,464
[45] Date of Patent: Sep. 26, 2000

[54] PROCESS FOR THE PREPARATION OF A MAGNESIUM SALT OF A SUBSTITUTED SULFINYL HETEROCYCLE

[75] Inventors: Jan-Åke Högberg, Södertälje; Panagiotis Ioannidis, Spånga; Anders Mattson, Täby, all of Sweden

[73] Assignee: Astra Aktiebolag, Sodertalje, Sweden

[21] Appl. No.: 08/860,825

[22] PCT Filed: Apr. 22, 1997

[86] PCT No.: PCT/SE97/00674

§ 371 Date: Jul. 10, 1997

§ 102(e) Date: Jul. 10, 1997

[87] PCT Pub. No.: WO97/41114

PCT Pub. Date: Nov. 6, 1997

[30] Foreign Application Priority Data

Apr. 26, 1996 [SE] Sweden .................................. 9601598

[51] Int. Cl.⁷ .................................................. C07D 401/12
[52] U.S. Cl. ..................... 546/273.7; 546/118; 548/303.7
[58] Field of Search ................................ 546/273.7, 118; 548/303.7

[56] References Cited

U.S. PATENT DOCUMENTS

| | | | |
|---|---|---|---|
| 4,563,455 | 1/1986 | Ueda et al. .............................. | 514/338 |
| 4,738,974 | 4/1988 | Brandstrom .............................. | 514/338 |
| 4,851,419 | 7/1989 | Cox et al. ................................ | 514/338 |
| 5,391,752 | 2/1995 | Hoerrer et al. .......................... | 514/338 |
| 5,690,960 | 11/1997 | Bengtsson et al. ...................... | 424/480 |
| 5,693,818 | 12/1997 | Von Unge ................................ | 514/338 |
| 5,714,504 | 2/1998 | Lindberg et al. ........................ | 514/338 |

FOREIGN PATENT DOCUMENTS

| | | |
|---|---|---|
| 0201094 | 12/1986 | European Pat. Off. . |
| 9427988 | 12/1994 | WIPO . |
| 9501977 | 1/1995 | WIPO . |
| 9601623 | 1/1996 | WIPO . |

OTHER PUBLICATIONS

Okabe et al. "Preparation of Benzimidazole Derivatives", Chem. Abs. 108: 683, 1988.

*Primary Examiner*—Jane Fan
*Attorney, Agent, or Firm*—White & Case LLP

[57] ABSTRACT

A novel process for the preparation of a magnesium salt of Formula I of a substituted sulfinyl heterocyclic compound containing an imidazole moiety. The process is carried out by mixing the substituted heterocycle of formula I with a weak and a magnesium source. The base and the magnesium source are selected to result in residues which are easy to remove during the reaction. The invention also relates to the use of the produced compounds in medicine.

8 Claims, No Drawings

PROCESS FOR THE PREPARATION OF A MAGNESIUM SALT OF A SUBSTITUTED SULFINYL HETEROCYCLE

This is a 371 of PCT/SE97/00674 Apr. 22, 1997 now WO 97/41114 Nov. 6, 1997.

FIELD OF THE INVENTION

The present invention relates to a novel process for the preparation of magnesium salts of substituted sulfinyl heterocyclic compounds containing an imidazole moiety as well as the use of the produced magnesium salts in medicine. More particularly, the present invention relates to the preparation of magnesium salts of substituted benzimidazoles such as the magnesium salts of omeprazole and of its single enantiomers.

BACKGROUND OF THE INVENTION AND PRIOR ART

Substituted benzimidazoles such as for instance the compounds with the generic names omeprazole, lansoprazole, pantoprazole, pariprazole and leminoprazole have properties making the compounds useful as inhibitors of gastric acid secretion. This class of compounds is known as proton pump inhibitors of $H^+K^+$ATPase inhibitors. There are a large number of patents and patent applications disclosing such proton pump inhibitors and processes for their preparation.

There is a general need in industry that pharmaceutically active compounds should be produced by processes giving products with properties making them suitable for pharmaceutical preparations, such as being easy to handle in a full scale production and having good storage stability.

WO 95/01977 discloses a novel magnesium salt of omeprazole with a specific degree of crystallinity making the product suitable for pharmaceutical formulations. The novel product is prepared by a process comprising the following steps; reacting omeprazole with magnesium alcoholate; separating inorganic salts from the reaction mixture; crystallizing the magnesium salt of omeprazole and isolating the product. The magnesium alcoholate is formed from metallic magnesium which requires special process conditions. The use of magnesium alcoholate in the process constitutes a potential difficulty with the formation of relatively insoluble magnesium salts, such as magnesium hydroxide. Filtration of such magnesium hydroxide is complicated because of gelling and extremely small particle size. The prior process is rather complicated, is water sensitive and requires special conditions. The prior process also has a large equipment requirement in the form of three reaction vessels and a separator. Therefore, there is a need for a more efficient process resulting in shorter manufacturing time, less reaction equipment and giving a higher yield pro volume.

The present invention provides improvements over the process disclosed in WO 95/01977 for the preparation of the magnesium salts of omeprazole and of other substituted benzimidazoles. Process for the preparation of certain salts of the single enantiomers of omeprazole, such as the magnesium salts, and processes for their preparation are described in EP 94917244.9.

As discussed in WO 95/01783 the magnesium salts of proton pump inhibitors, such as the magnesium salt of omeprazole, are especially suitable for the manufacturing of pharmaceutical formulations, such as tablets. The magnesium salts are stable, they may be easily purified by crystallization, and are easy to handle in pharmaceutical procedures and processes.

SUMMARY OF THE INVENTION

The present invention provides a novel process for the preparation of magnesium salts of substituted sulfinyl heterocycles containing an imidazole moiety and especially of substituted benzimidazole derivatives. The process results in a high yield pro volume, requires less equipment, is less time consuming, environmental friendly and more economically efficient than processes described in the above mentioned patent applications. According to the novel process a magnesium salt of a substituted sulfinyl heterocycle containing an imidazole moiety is prepared by mixing the substituted sulfinyl heterocycle containing an imidazole moiety with a weak base, preferably an amine or ammonia, and a magnesium source, such as an organic or inorganic magnesium salt or a combination of such salts. By the novel process of the present invention formation of magnesium hydroxide is avoided, for example in the preparation of omeprazole magnesium salt.

Alternatively, the process may also be used to prepare other salts of a substituted sulfinyl heterocycle containing an imidazole moiety, for instance multiple valent salts, such as calcium salts.

DETAILED DESCRIPTION OF THE INVENTION

The present invention provides a novel method of preparing a magnesium salt of a substituted sulfinyl heterocycle containing an imidazole moiety with the following formula I.

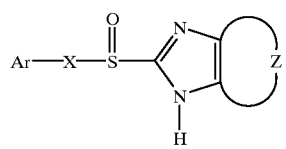

wherein

Ar is

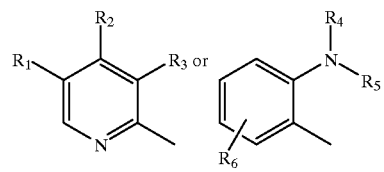

Z is

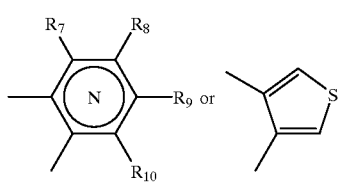

and X is

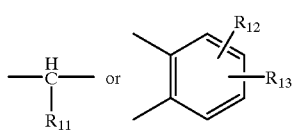

wherein

N inside the benzene ring of the benzimidazole moiety means that one of the carbon atoms substituted by $R_7$–$R_{10}$ optionally may be exchanged for a nitrogen atom without any substituents;

$R_1$, $R_2$ and $R_3$ are the same or different and selected from hydrogen, alkyl, alkylthio, alkoxy optionally substituted by fluorine, alkoxyalkoxy, dialkylamino, piperidino, morpholino, halogen, phenylalkyl and phenylalkoxy; wherein alkyl and alkoxy groups may be branched or linear and may comprise cyclic alkyl groups such as cykloalkylalkoxy groups.

$R_4$ and $R_5$ are the same or different and selected from hydrogen, alkyl and aralkyl;

$R_6$ is hydrogen, halogen, trifluoromethyl, alkyl and alkoxy;

$R_7$–$R_{10}$ are the same or different and selected from hydrogen, alkyl, alkoxy, halogen, haloalkoxy, alkylcarbonyl, alkoxycarbonyl, oxazolyl, trifluoroalkyl, or adjacent groups $R_7$–$R_{10}$ form ring structures which may be further substituted;

$R_{11}$ is hydrogen or forms an alkylene chain together with $R_3$ and $R_{12}$ and $R_{13}$ are the same or different and selected from hydrogen, halogen, alkyl or alkoxy groups, wherein alkoxy groups may be branched or straight $C_1$–$C_9$- chains and the alkyl and alkoxy groups may comprise cyclic alkyl groups, for example cycloalkylalkyl.

Preferably, the substituted sulfinyl heterocyclic compound containing an imidazole moiety prepared by the novel method is a magnesium salt of formula I'.

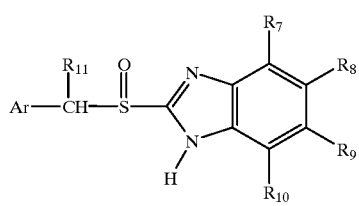

(I')

wherein
Ar is

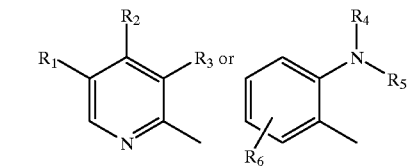

and $R_1$–$R_{11}$ are as defined above in connection with formula I.

Most preferably the compounds prepared by the novel process are any of the formulas Ia to Ih.

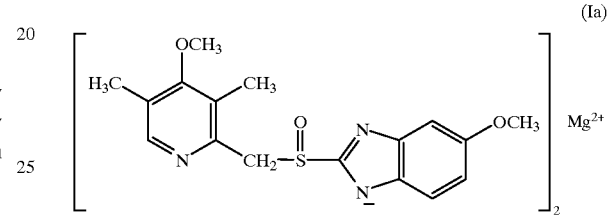

(Ia)

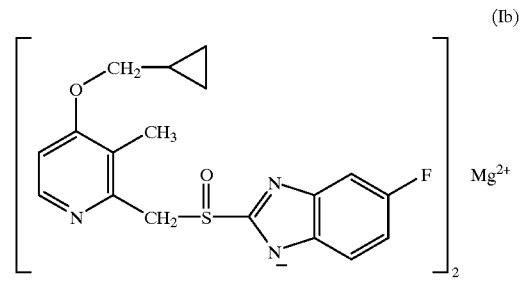

(Ib)

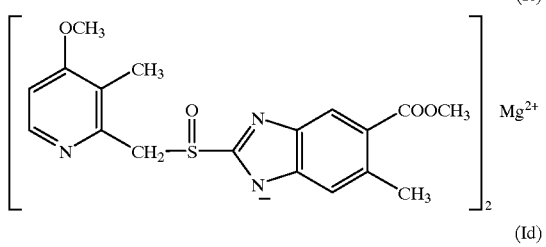

(Ic)

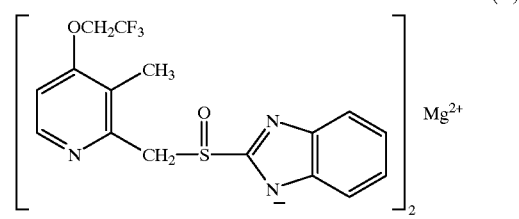

(Id)

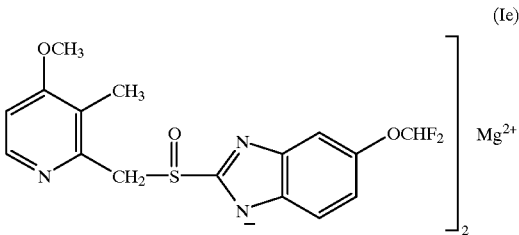

(Ie)

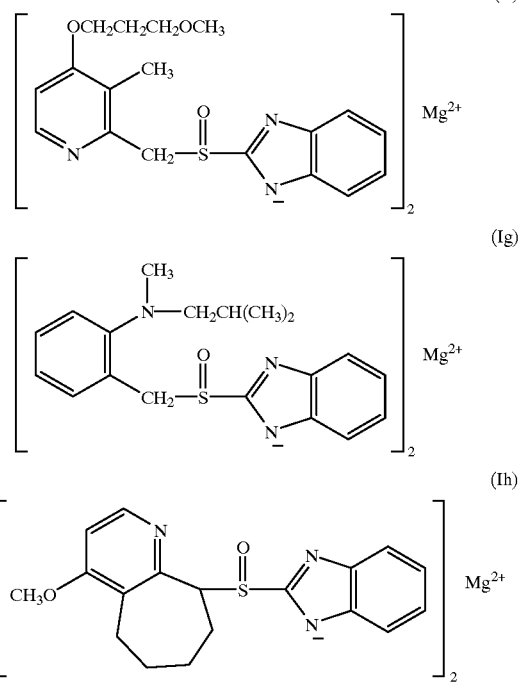

The substituted sulfinyl heterocycle of Formula I is mixed/reacted with a weak base and a magnesium source and optionally in the presence of an organic solvent. After the reaction is completed, the mixture is clarified, if needed. The product is preferably precipitated from the filtrate, optionally, by the addition of an appropriate solvent, for instance water or acetone, which facilities the precipitation of the product. As an additional benefit, when water is used, the solubility of the inorganic salts is enhanced resulting in less impurities in the form of inorganic salts in the obtained product. The obtained product may be further processed by recrystallization.

The novel process according to the present invention may be exemplified by the following reaction scheme showing a reaction between a substituted benzimidazole (HA) and a weak base (B) in the presence of a magnesium source ($Mg_mX_n$).

$$2HA + 2B \xrightarrow{\frac{1}{m}(Mg_mX_n)} MgA_2 + \frac{n}{m}\left[(HB)\frac{2m}{n} \cdot X\right]$$

In the above formula, wherein HA is a substituted benzimidazole, H denotes the most acidic proton in said compound, B is a weak base and X is a counterion to $Mg^{2+}$ in the magnesium source ($Mg_mX_n$).

The base used in the reaction must not be toxic or it should only have a low toxicological effect. It shall preferably be a weak base to minimize precipitation of poorly soluble inorganic magnesium salts, such as magnesium hydroxide during the reaction sequence. Such precipitation of, for instance, magnesium hydroxide—is normally difficult to remove during the process and in the final product. With the expression weak base is meant a base with a pKa lower than alkoxides and hydroxides, but higher than the substituted sulfinyl heterocycles of the present invention, preferably with a pKa from 7–12. More preferably the weak base is an organic amine or ammonia. With respect to environmental aspects the base shall preferably be one resulting in residues in the form of ammonium salts which easily can be isolated, for example by filtration or centrifugation, in order to minimize effluent of nitrogen based pollutants, such as ammonia.

The magnesium source may be an organic as well as an inorganic magnesium salt, such as magnesium acetate, magnesium nitrate, magnesium sulfate, magnesium carbonates and magnesium chloride, preferably magnesium sulfate.

If a solvent is used in the reaction, it is preferably one which can be used throughout the complete process. Such a solvent is preferably an alcohol, for instance methanol.

The process is not temperature sensitive and it may be carried out at ambient temperature. Of course the process temperature and time may be adjusted with respect to the quality and yield of the obtained product.

The new process according to the present invention may be exemplified in more general terms by the manufacture of omeprazole magnesium salt.

Omeprazole magnesium salt may be formed in accordance with the invention by treating a weight amount of omeprazole with weighed amounts of aqueous ammonia and magnesium sulfate in methanol.

The order of charging the different reactants is not critical for the produced product. A specific order may be preferred with respect to the equipment actually used in the factory.

The temperature may be $-10°$ C. to $+50°$ C. and preferably is between $0°$ C. and ambient temperature. After termination of the reaction, the resulting inorganic magnesium salts are separated off in a suitable equipment, such as a centrifuge or a pressure filter.

The temperature of the clear solution is adjusted to $-10°$ C. to $+40°$ C., preferably $10°$ C. to $35°$ C. The solution may be seeded with omeprazole magnesium salt crystals and an amount of water is added to start the precipitation. The amount of water is not critical, but can be equal to or less than the volume of the solution; preferably the latter.

The formed crystalline product is separated from the mother liquid (filtrate), for instance by centrifugation or filtration. Other suitable procedures may be used to separate the product. The produced crystalline product is washed with aqueous methanol and dried under reduced pressure and heat.

The process according to the present invention is described in more detail by the following examples, which are not intended to limit the scope of the invention.

EXAMPLES

Example 1

Preparation of 5-methoxy-2[[(4-methoxy-3,5-dimethyl-2-pyridinyl)methyl]sulfinyl]-1H-benzimidazole, magnesium salt.

5-Methoxy-2[[(4-methoxy-3,5-dimethyl-2-pyridinyl)methyl]sulfinyl]-1H-benzimidazole (31.6 kg, 91.6 mol) together with aqueous $NH_3$ (7.4 kg, 107 mol) was added to methanol (212 l). To the obtained mixture $MgSO_4 \times 7\ H_2O$ (17.6 kg, 69.9 mol) was added at ambient temperature. After the reaction was completed inorganic salts were removed by means of filtration. Water was added to the filtrate, the mixture was clarified and water (91 l) was added. The mixture was kept for stirring in order to crystallize the product. The obtained product was centrifuged and was washed with a mixture of MeOH/water. The product was dried at reduced pressure at 40° C. Yield: 71%. (Mg content: found 3.47%, Theoretically calculated 3.41%)

The % crystallinity of the obtained product was measured with powder X-ray diffraction (XRD) as described below: A thin layer of the triturated sample was smeared onto a cut silicon single crystal zero background holder which was rotated during the measurement. Cu Kα radiation and constant or automatic antiscatter and divergence slits were used to obtain a diffraction from 1 to 2° 2θ to at least 35°.

The % crystallinity was calculated with the formula $$\% \ crystallinity = 100 * C/(A+C)$$

C=the area from the peaks in the diffractogram ("the crystalline area"),

A=the area between the peaks and the background ("the amorphous area").

Area calculations were performed between 4–33° 2θ. The lowest intensity value found in this interval was chosen as the constant background and subtracted from the area A. When constant slits were used the increased background at low angles due to the influence from the primary beam was also subtracted from the area A.

The crystallinity was measured to be 80±5% (calculation interval 4–33°).

Example 2

Preparation of 5-methoxy-2[[(4-methoxy-3,5-dimethyl-2-pyridinyl)methyl]sulfinyl]-1H-benzimidazole, magnesium salt.

5-Methoxy-2[[(4-methoxy-3,5-dimethyl-2-pyridinyl) methyl]sulfinyl]-1H-benzimidazole (25 g, 72.4 mmol) together with isopropylamine (7.4 ml, 86.9 mmol) was added to methanol (100 ml). To the obtained mixture $MgSO_4 \times 7 \ H_2O$ (8.85 g, 35.9 mmol) was added at ambient temperature. After the reaction was completed inorganic salts were removed by means of filtration. Water was added to the filtrate, the mixture was clarified and water (100 ml) was added dropwise. The product was filtered off and was washed with a mixture of MeOH/water (50 ml, 1:1). The product was dried at reduced pressure overnight. Yield: 95%. (Mg-content: 3.41; calculated theoretically 3.41).

Example 3

Preparation of 5-methoxy-2[[(4-methoxy-3,5-dimethyl-2-pyridinyl)methyl]sulfinyl]-1H-benzimidazole, magnesium salt.

5-Methoxy-2[[(4-methoxy-3,5-dimethyl-2-pyridinyl) methyl]sulfinyl]-1H-benzimidazole (25 g, 72.4 mmol) together with isopropylamine (7.4 ml, 86.9 mmol) was added to methanol (100 ml). To the obtained mixture $Mg(O_{Ac})_2 \times 4 \ H_2O$ (9.34 g, 43.6 mmol) was added at ambient temperature. After the radiation was completed inorganic salts were removed by means of filtration. Water was added to the filtrate, the mixture was clarified and water (100 ml) was added dropwise. The obtained product was filtered off and was washed with a mixture of MeOH/water (50 ml, 1:1). The product was dried at reduced pressure overnight. Yield: 92%. (Mg content: 3.42; calculated theoretically: 3.41)

Example 4

Preparation of 5-methoxy-2[[(4-methoxy-3,5-dimethyl-2-pyridinyl)methyl]sulfinyl]-1H-benzimidazole, magnesium salt.

5-Methoxy-2[[(4-methoxy-3,5-dimethyl-2-pyridinyl) methyl]sulfinyl]-1H-benzimidazole (25 g, 72.4 mmol) together with isopropylamine (7.4 ml, 86.9 mmol) was added to methanol (100 ml). To the mixture $Mg(NO_3)_2 \times 6 \ H_2O$ (11.2 g, 43.7 mmol) was added at ambient temperature. After the reaction was completed inorganic salts were removed by means of filtration. Water was added to the filtrate, the mixture was filtered and the filter cake was washed with methanol (10 ml). Water (100 ml) was added dropwise to the combined organic layers. The product was filtered off and was washed with a mixture of MeOH/water (50 ml, 1:1). The product was dried overnight. Yield: 89%. (Mg content: 3.39; calculated theoretically: 3.41))

Example 5

Preparation of 5-methoxy-2[[(4-methoxy-3,5-dimethyl-2-pyridinyl)methyl]sulfinyl]-1H-benzimidazole, magnesium salt.

5-Methoxy-2[[(4-methoxy-3,5-dimethyl-2-pyridinyl) methyl]sulfinyl]-1H-benzimidazole (1.0 g, 2.9 mmol) together with diethylamine (0.35 ml, 3.4 mmol) were added to methanol (9 ml). To the obtained mixture $MgCl_2$ (142 mg, 1.5 mmol) in methanol (2 ml) was added at ambient temperature. Water (6.5 ml) was added dropwise. The obtained product was filtered off and was washed with a mixture of MeOH/water (20 ml, 1:1). Yield: 76%. (Mg content: 3.38; calculated theoretically: 3.41)

Example 6

Preparation of (−)-5-fluoro-2-[[(4-cyclopropylmethoxy-2-pyridinyl)methyl]sulfinyl]-1H-benzimidazole, magnesium salt.

(−)-5-Fluoro-2[[(4-cyclopropylmethoxy-2-pyridinyl) methyl]sulfinyl]-1H-benzimidazole (20 g, 57.9 mmol) together with $NH_3$ (7.5 ml, 100.2 mmol) was added to methanol (80 ml). To the mixture of $MgSO_4 \times 7 \ H_2O$ (11.4 g, 45.3 mmol) was added at ambient temperature. The mixture was clarified. Water (8 ml) was added dropwise during rapid stirring. Another portion of water (72 ml) was added dropwise for 75 minutes. The mixture was stirred for 50 minutes while the product precipitated. The product was filtered off and was washed with a mixture of MeOH/water (2 ml, 1:1). The product was dried at reduced pressure at 35° C. overnight. Yield: 61%. (Mg content: 3.40; calculated theoretically: 3.41).

Example 7

Preparation of 5-fluoro-2[[(4-cyclopropylmethoxy-2-pyridinyl)methyl]sulfinyl]-1H-benzimidazole, magnesium salt.

5-Fluoro-2[[(4-cyclopropylmethoxy-2-pyridinyl)methyl] sulfinyl]-1H-benzimidazole (10 g, 28.9 mmol) together with isopropylamine (1.71 g, 28.9 mmol) was added to methanol (40 ml). To the obtained mixture MgCl$_2$ (1.35 g, 14 mmol) was added at ambient temperature. Excess of amine was evaporated off. The mixture was clarified and water (56.5 ml) was added dropwise. The mixture was cooled to 20° C. and the product was filtered off and was washed with a mixture of MeOH/water (20 ml, 3:1). The obtained product was dried at reduced pressure at 50° C. overnight. Yield: 86%. (Mg content: 3.42; calculated theoretically: 3.41)

Example 8

Preparation of 5-fluoro-2[[(4-cyclopropylmethoxy-2-pyridinyl)methyl]sulfinyl]-1H-benzimidazole, magnesium salt.

5-Fluoro-2[[(4-cyclopropylmethoxy-2-pyridinyl)methyl] sulfinyl]-1H-benzimidazole (690 g, 1.97 mol) together with aqueous NH$_3$ (140 ml; 2.17 mol) was added to methanol (2.4l). To the obtained mixture MgCl$_2$ (105.2 g, 1.08 mol) in methanol (940 ml) was added. The mixture was clarified and water (350 ml) was added during rapid stirring. Another portion of water (3.15 l) was added and the mixture was stirred overnight. The product was filtered off and was washed with a mixture of MeOH/water (1 l, 4:1). Yield: 91%. (Mg content: 3.46; calculated theoretically: 3.41)

Example 9

Preparation of (−)-5-methoxy-2-[[(4-methoxy-3,5-dimethyl-2-pyridinyl)methyl]sulfinyl]-1-H-benzimidazole, magnesium salt (3l)-5-Methoxy-2-[[(4-methoxy-3,5-dimethyl-2-pyridinyl)methyl]sulfinyl]-1H-benzimidazole (10.6 g, 29 mmol) together with aqueous ammonia (3.8 ml of 25%, 50 mmol) was added to methanol (40 ml). To the solution MgSO$_4$×7 H$_2$O (5.7 g, 23 mmol) was added. After stirring for 10 minutes the mixture was filtered and the filtrate was diluted with methanol (60 ml). Acetone (150 ml) was added and the solution was seeded with crystals while stirring. After 14 hours the product was isolated by filtration and the crystals were washed with methanol/acetone (50 ml). The product was dried over night. Yield: 41%. (Mg-content: found 3.33%, Calculated for (C$_{17}$H$_{18}$N$_3$O$_3$S)$_2$Mg 3.41%).

Example 10

Preparation of 5-difluoromethoxy-2-[[(3,4-dimethoxy-2-pyridinyl)methyl]sulfinyl]-1H-benzimidazole, magnesium salt 5-Difluoromethoxy-2-[[(3,4-dimethoxy-2-pyridinyl) methyl]sulfinyl]-1H-benzimidazole (11.1 g, 29 mmol) together with aqueous ammonia (3.8 ml of 25%, 50 mmol) was added to methanol (60 ml). To the solution MgSO$_4$×7 H$_2$O (5.7 g, 23 mmol) was added. After stirring for 3 minutes the mixture was filtered. Water (40 ml) was added dropwise to the filtrate while stirring. After 30 minutes the product was isolated by filtration and the crystals were washed with methanol/water (25 ml). The product was dried under reduced pressure. Yield: 67%. (Mg-content: found 3.07%, Calculated for (C$_{16}$H$_{14}$N$_3$O$_4$S)$_2$Mg 3.08%).

The best mode to practice the invention at present is by the process described in Example 1.

What is claimed is:

1. An improved process for the preparation of a magnesium salt of a substituted sulfinyl heterocyclic compound containing an imidazole moiety according to Formula I

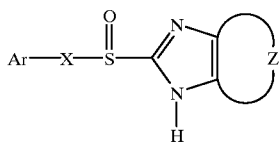

wherein
Ar is

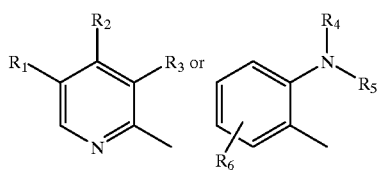

Z is

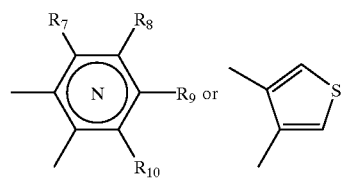

X is

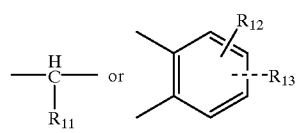

wherein
N inside the benzene ring of the benzimidazole moiety means that one of the carbon atoms substituted by R$_7$–R$_{10}$ optionally may be exchanged for a nitrogen atom without any substituents;

R$_1$, R$_2$ and R$_3$ are the same or different and are selected from the group consisting of hydrogen, alkyl, alkylthio, alkoxy, fluorine-substituted alkoxy, alkoxyalkoxy, dialkylamino, piperidino, morpholino, halogen, phenylalkyl and phenylalkoxy, wherein alkyl and alkoxy groups may be branched or linear or contain a cyclic alkyl group;

R$_4$ and R$_5$ are the same or different and are selected from the group consisting of hydrogen, alkyl and aralkyl;

R$_6$ is selected from the group consisting of hydrogen, halogen, trifluoromethyl, alkyl and alkoxy;

R$_7$–R$_{10}$ are the same or different and are selected from the group consisting of hydrogen, alkyl, alkoxy, halogen, haloalkoxy, alkylcarbonyl, alkoxycarbonyl, oxazolyl, and trifluoroalkyl;

R$_{11}$ is hydrogen; and

R$_{12}$ and R$_{13}$ are the same or different and are selected from the group consisting of hydrogen, halogen, alkyl or alkoxy groups, wherein alkoxy groups may be branched or straight C$_1$–C$_9$ chains or contain a cyclic alkyl group, wherein the improvement is mixing the substituted sulfinyl heterocycle of Formula I with a weak base selected from the group consisting of lower alkyl amines, di-lower alkyl amines, tri-lower alkyl amines and ammonia and a magnesium source selected from the group consisting of magnesium acetate, magnesium nitrate, magnesium sulfate, magnesium carbonate and magnesium chloride.

2. The process according to claim 1, wherein the weak base is ammonia.

3. The process according to claim 1, wherein the reaction is carried out in the presence of a solvent.

4. The process according to claim 1, wherein the reaction is carried out in the presence of an aqueous organic solvent.

5. The process according to claim 1, wherein the weak base and magnesium source are selected to give an ammonium salt which can be removed by filtration during said process.

6. The process according to claim 1, wherein the magnesium salt of 5-Methoxy-2[[(4-methoxy-3,5-dimethyl-2-pyridinyl)methyl]sulfinyl]-1H-benzimidazole is prepared.

7. The process according to claim 1, wherein the magnesium salt of (−)-5-Methoxy-2[[(4-methoxy-3,5-dimethyl-2-pyridinyl)methyl]sulfinyl]-1H-benzimidazole is prepared.

8. The process according to claim 1, wherein any of the alkyl and alkoxy groups of $R_1$, $R_2$, $R_3$, $R_{12}$ and $R_{13}$ contain a cyclic alkyl group.

* * * * *

UNITED STATES PATENT AND TRADEMARK OFFICE
CERTIFICATE OF CORRECTION

PATENT NO : U.S. Patent No. 6,124,464
DATED : September 26, 2000
INVENTOR(S): Hogberg et al.

It is certified that error appears in the above-identified patent and that said Letters Patent are hereby corrected as shown below:

In claim 1, col. 10, line 35, delete " 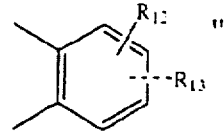 "

and insert therefor -- 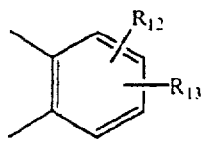 --.

Signed and Sealed this

Seventeenth Day of April, 2001

*Attest:*

NICHOLAS P. GODICI

*Attesting Officer*     *Acting Director of the United States Patent and Trademark Office*